(12) United States Patent
Derouault et al.

(10) Patent No.: US 12,076,094 B2
(45) Date of Patent: Sep. 3, 2024

(54) FLUOROSCOPIC ROBOTIC PROSTHETIC IMPLANT SYSTEM AND METHODS

(71) Applicant: Orthosoft ULC, Montreal (CA)

(72) Inventors: Quentin Derouault, Montreal (CA); Julie Deslongchamps, Brossard (CA); Jerome Harrison, Montreal (CA); Richard Moussa, Montreal (CA); Chloe Landry, Saint-Jean-sur-Richelieu (CA)

(73) Assignee: Orthosoft ULC, Montreal (CA)

( * ) Notice: Subject to any disclaimer, the term of this patent is extended or adjusted under 35 U.S.C. 154(b) by 185 days.

(21) Appl. No.: 17/892,808

(22) Filed: Aug. 22, 2022

(65) Prior Publication Data

US 2023/0068971 A1 Mar. 2, 2023

Related U.S. Application Data

(60) Provisional application No. 63/293,350, filed on Dec. 23, 2021, provisional application No. 63/239,643, filed on Sep. 1, 2021.

(51) Int. Cl.
*A61B 34/20* (2016.01)
*A61B 34/10* (2016.01)

(52) U.S. Cl.
CPC .............. *A61B 34/20* (2016.02); *A61B 34/10* (2016.02); *A61B 2034/2055* (2016.02)

(58) Field of Classification Search
CPC . A61B 34/20; A61B 34/10; A61B 2034/2055; A61B 2090/376; A61B 34/32;
(Continued)

(56) References Cited

U.S. PATENT DOCUMENTS 8,884,618 B2 11/2014 Mahfouz
9,675,461 B2 6/2017 Mahfouz
(Continued)

FOREIGN PATENT DOCUMENTS

AU 2022221537 12/2023
EP 2956046 5/2018
(Continued)

OTHER PUBLICATIONS

"European Application Serial No. 22193190.0, Extended European Search Report mailed Jan. 24, 2023", 5 pgs.
(Continued)

*Primary Examiner* — Bo Joseph Peng
(74) *Attorney, Agent, or Firm* — Schwegman Lundberg & Woessner, P.A.

(57) ABSTRACT

Techniques for robotically guiding a cup-shaped implant or instrument are provided. In an example, the technique can include a combination of the following operations. Acquiring a calibration image including a cup-shaped element in a first orientation. Identifying a first elliptical outline of the cup-shaped element. Acquiring a navigation image including the cup-shaped element in a second orientation. Identifying a second elliptical outline of the cup-shaped element. Aligning a coordinate system of a robotic system to a patient, and positioning an implant or instrument based on a pre-operative plan within the coordinate system.

20 Claims, 10 Drawing Sheets

(58) Field of Classification Search
CPC . A61B 34/37; A61B 90/37; A61B 2034/2065; A61B 2034/2074
See application file for complete search history.

(56) References Cited

U.S. PATENT DOCUMENTS

| | | | |
|---|---|---|---|
| 11,259,874 B1* | 3/2022 | Landon | G16H 40/67 |
| 2004/0171924 A1* | 9/2004 | Mire | A61B 34/20 |
| | | | 600/407 |
| 2008/0056552 A1 | 3/2008 | Muller | |
| 2008/0262812 A1* | 10/2008 | Arata | A61B 90/36 |
| | | | 703/11 |
| 2012/0209277 A1* | 8/2012 | Leparmentier | A61B 34/76 |
| | | | 606/91 |
| 2017/0258526 A1* | 9/2017 | Lang | A61B 17/155 |
| 2019/0000578 A1* | 1/2019 | Yu | A61B 34/10 |
| 2019/0005848 A1* | 1/2019 | Garcia Kilroy | G16H 40/67 |
| 2019/0133689 A1* | 5/2019 | Johnson | G09B 9/00 |
| 2019/0231446 A1* | 8/2019 | Bowling | A61B 34/30 |
| 2019/0388099 A1* | 12/2019 | Zuhars | A61B 90/39 |
| 2020/0069280 A1* | 3/2020 | Behzadi | A61F 2/28 |
| 2020/0138518 A1* | 5/2020 | Lang | A61B 90/37 |
| 2021/0353431 A1* | 11/2021 | Wilde | A61B 34/32 |
| 2022/0218422 A1* | 7/2022 | Khurana | A61B 34/76 |

FOREIGN PATENT DOCUMENTS

| | | |
|---|---|---|
| EP | 3331440 | 6/2020 |
| EP | 3821844 | 5/2021 |
| JP | 2023036040 | 3/2023 |
| JP | 7331223 | 8/2023 |
| JP | 2023144011 | 10/2023 |
| WO | 2019079521 | 4/2019 |

OTHER PUBLICATIONS

"Australian Application Serial No. 2022221537, First Examination Report mailed Sep. 4, 2023", 3 pgs.

"Australian Application Serial No. 2022221537, Response filed Oct. 31, 2023 to First Examination Report mailed Sep. 4, 2023", 3 pgs.

"Australian Application Serial No. 2022221537, Response Filed Oct. 31, 2023 to First Examination Report mailed Sep. 4, 2023", No Amendments, 1 pg.

"Canadian Application Serial No. 3, 171,637, Examiners Rule 86(2) Report mailed Nov. 28, 2023", 5 pgs.

* cited by examiner

FLUOROSCOPIC ROBOTIC PROSTHETIC IMPLANT SYSTEM AND METHODS

CLAIM OF PRIORITY

This application claims the benefit of U.S. Provisional Patent Application Ser. No. 63/239,643, filed on Sep. 1, 2021, and also claims the benefit of U.S. Provisional Patent Application Ser. No. 63/293,350, filed on Dec. 23, 2021, the benefit of priority of each of which is claimed hereby, and each of which is incorporated by reference herein in its entirety.

FIELD OF THE DISCLOSURE

The present document relates to robotic surgery techniques, and more particularly, to techniques for implanting a prosthesis with robotic assistance.

BACKGROUND OF THE DISCLOSURE

The use of robotics in surgery is on the rise. Total hip arthroplasty surgeries are performed almost half a million times a year in the United States. In some cases, the surgeries are performed with assistance from a surgical robot. During robotically assisted surgeries, an optical navigation system is typically used to track location of the robotic arm and/or the patient. Optical navigation systems can introduce challenges into the operating room environment due to the need for additional equipment space and sight line limitations to ensure the navigation system can visualize the necessary instruments and/or patient anatomy. Optical navigation systems also do not typically remove the need for intra-operative imaging, such as fluoroscopy, to validate implant positioning and other related uses.

SUMMARY OF THE DISCLOSURE

Techniques and systems for robotically assisted prosthesis positioning and implantation are provided. The invention is discussed in view of Total Hip Arthroplasty (THA) and more specifically in view of implantation of a prosthetic acetabular cup in the acetabulum of a patient. However, the disclosure is applicable to robotically assisted implantation of any cup-shaped implant. Further, the systems and techniques discussed herein can be adapted for use in implanting other prosthetic devices.

In an example, the robotic surgical system (system) discussed herein is used to assist surgeons in performing THA with features to assist with acetabular shell (cup) impaction for a direct anterior approach. The robotic surgical system uses fluoroscopic images to determine the orientation of the impaction instrument in relation to patient anatomy and as a guide for acetabular component orientation. The system allows the surgeon to input surgical pre-operative planning values and preview the acetabular component orientation intra-operatively. Throughout the surgical workflow, fluoroscopic images are acquired with a C-Arm (e.g., a special type of intra-operative fluoroscope capable of capturing fluoroscopic images of a patient on an operating table). Fluoroscopic images are then captured with a hand-held computing device that interoperates with the robotic platform to facilitate intraoperative planning and execution of the surgical procedure. The current orientation of the impaction instrument is computed from the image capture and is adjusted to match the pre-operative plan using the robotic platform, which can position the impaction instrument automatically as well as cooperatively with the surgeon. The inventors have developed algorithms to determine orientation of the implant and navigate the impaction instrument without the need for external optical navigation. The robotic platform positions the impaction instrument and implant then maintains those positions during impaction of the acetabular cup (implant) into the anatomy. The intra-operative workflow and surgical concepts implemented in the system operate to augment, rather than disrupt, the THA direct anterior approach workflow. As such, at the time of the surgery, the system assists the surgeon in (1) determining reference alignment axes and cup orientation using image-to-image and robotic registration, (2) precisely orienting the cup inserter relative to the desired orthopedic implant angle by using a Robotic Arm, and (3) providing leg length and offset discrepancies measurements based on fluoroscopic image references.

This section is intended to provide an overview of subject matter of the present patent application. It is not intended to provide an exclusive or exhaustive explanation of the invention. The detailed description is included to provide further information about the present patent application.

Figure 1:
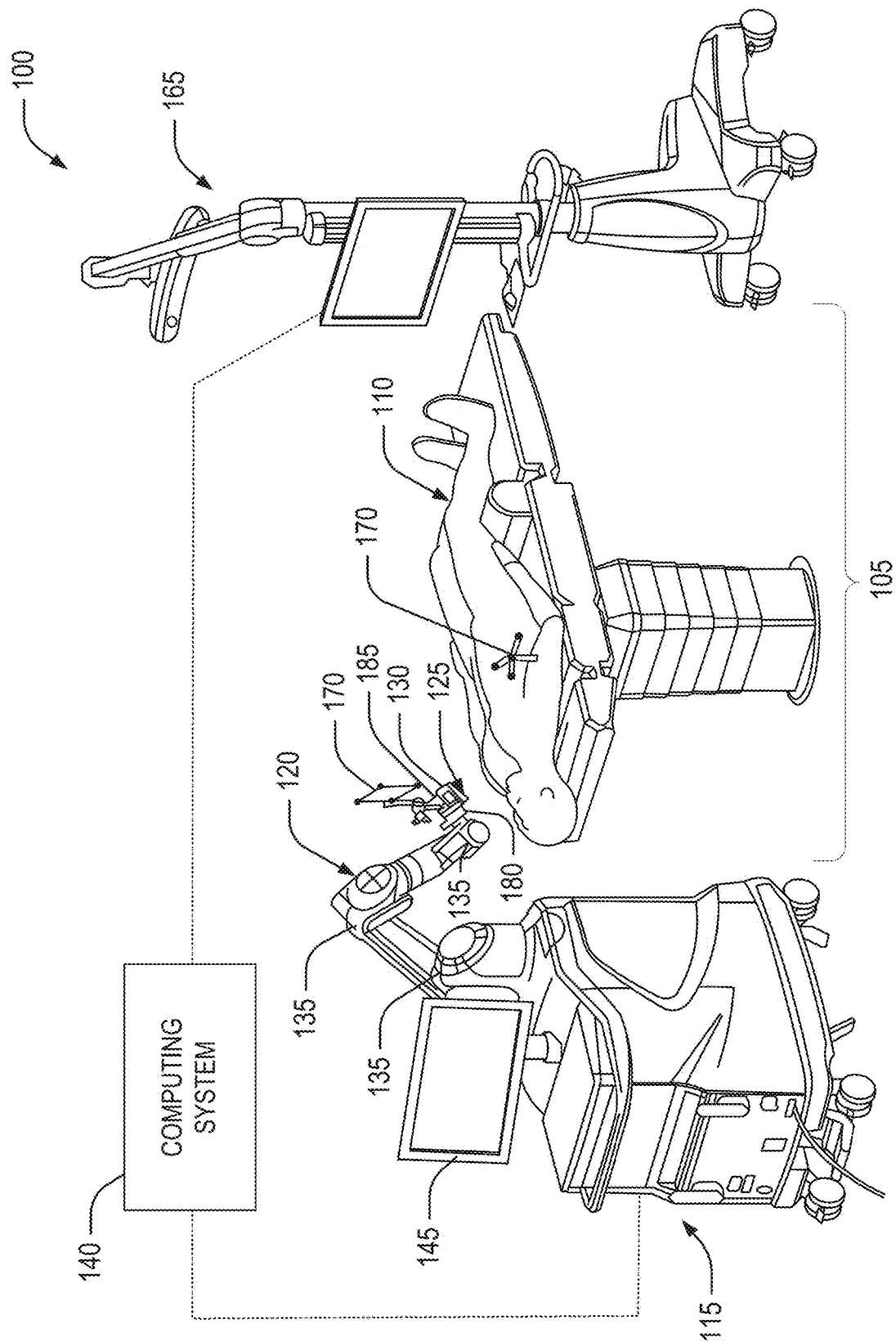
FIG. 1 is a diagrammatic view of an operating room including a robot-assisted surgical system comprising a robotic arm, a computing system and a tracking system.

In the drawings, which are not necessarily drawn to scale, like numerals may describe similar components in different views. Like numerals having different letter suffixes may represent different instances of similar components. The drawings illustrate generally, by way of example, but not by way of limitation, various embodiments discussed in the present document.

DETAILED DESCRIPTION

Example of the present disclosure provide systems and techniques for robotically assisted fluoroscopic implant positioning and impaction. A total hip replacement procedure, or total hip arthroplasty, can involve making an access incision in a hip region of a patient. Various surgical instruments configured for intra-procedurally reaming, cutting, broaching, impacting, or otherwise preparing bone surfaces of a patient during total hip arthroplasty are inserted through the incision, such as to access the proximal femur or the acetabular cup. Preparation of the acetabular cup often involves impacting the acetabular cup with the impactor, such as to insert or otherwise install an implant by repeatedly striking the impactor with a mallet. In a traditional THA procedure, impacting the acetabular cup into the patient's acetabulum is done entirely by feel and success relies heavily on technique and skill of the surgeon. Issues with acetabular cup positioning (e.g., malposition of the implant) after impaction can led to negative outcomes, such as impingement or leg length issues or dislocation. Robotic THA system typically attempt to prevent acetabular cup positioning issues through use of optical navigation, but optical navigation system can be difficult to deal within the operating environment and add incremental cost to the robotic platform. Robotic, navigation and traditional THA procedures also can suffer from long operating times, line of sight issues, and may require the use of positioning pins inserted into the bone that can increase the risk of fracture or infections.

The present inventors have developed a robotically assisted system that can precisely orient a cup-shaped implant (e.g., control inclination and anteversion), such as an acetabular shell (cup), and enable impaction of the acetabular shell to a planned inclination and anteversion. The robotically assisted system discussed herein does not rely on optical navigation and augments a surgeon's skills to ensure proper implant alignment after impaction.

FIG. 1 is a diagrammatic view of an operating room including a robot-assisted surgical system 100 comprising a robotic arm, a computing system and a tracking system. The robot-assisted surgical system 100 is a traditional system that integrates an optical navigation system 165 to assist in tracking robotic arm 120 position and patient anatomy position.

The surgical system 100 assist in a surgical procedure on a surgical area 105 of a patient 110. The surgical area 105 can include a joint and/or a bone of the patient 110. The surgical area 105 can include any surgical area of the patient 110, including but not limited to the hip, knee, spine, and the like. The surgical system 100 also includes a robotic system 115 with one or more robotic arms, such as robotic arm 120. As illustrated, the robotic system 115 will commonly utilize only a single robotic arm. The robotic arm 120 can be a 6 degree-of-freedom (DOF) robot arm, such as the ROSA® robot from Medtech, a Zimmer Biomet Inc. company. In some examples, the robotic arm 120 is cooperatively controlled with surgeon input on the end effector or surgical instrument, such as surgical instrument 125 (also referred to herein as end effector 125). In other examples, the robotic arm 120 can operate autonomously. While not illustrated in FIG. 1, one or more positionable surgical support arms can be incorporated into the surgical system 100 to assist in positioning and stabilizing instruments or anatomy during procedures.

Each robotic arm 120 rotates axially and radially and receives a surgical instrument, or end effector, 125 at a distal end 130. The surgical instrument 125 can be any surgical instrument adapted for use by the robotic system 115, such as a gripping device such as a pincer grip, a burring device, a reaming device, an impactor device such as an acetabular shell impactor, or the like. The surgical instrument 125 is positionable by the robotic arm 120, which includes multiple robotic joints, such as joint 135, that allows the surgical instrument 125 to be positioned at any desired location adjacent or within a given surgical area 105.

The robotic system 115 also includes a computing system 140 that operates the robotic arms 120 and surgical instrument 125. The computing system 140 can include at least a memory, processing unit, and user input devices, as will be described herein. The computing system 140 also includes a human interface device 145 for providing images for a surgeon to be used during surgery. The computing system 140 is illustrated as a separate standalone system, but in some examples the computing system 140 can be integrated into the robotic system 115. The human interface device 145 provides images, including but not limited to three dimensional images of bones, glenoid, joints, and the like. The human interface device 145 can include associated input mechanisms, such as a touch screen, foot pedals, or other input devices compatible with a surgical environment.

The computing system 140 can receive pre-operative medial images. These images are received in any manner and the images include, but are not limited to computed tomography (CT) scans, magnetic resonance imaging (MRI), two dimensional x-rays, three dimensional x-rays, ultrasound, and the like. These images in one example are sent via a server as files attached to an email. In another example the images are stored on an external memory device such as a memory stick and coupled to a USB port of the robotic system to be uploaded into the processing unit. In yet other examples, the images are accessed over a network by the computing system 140 from a remote storage device or service.

After receiving one or more images, the computing system 140 can generate one or more virtual models related to surgical area 105. Specifically, a virtual model of the patient's anatomy can be created by defining anatomical points (e.g., landmarks or anatomical landmarks) within the image(s) and/or by fitting a statistical anatomical model to the image data. The virtual model, along with virtual representations of implants, can be used for calculations related to the desired height, depth, inclination angle, or version (anteversion) angle of an implant, stem, surgical instrument, or the like related to be utilized in the surgical area 105. The virtual model can also be used to determine bone dimensions, implant dimensions, bone fragment dimensions, bone fragment arrangements, and the like. Any model generated, including three dimensional models, can be displayed on the human interface for reference during a surgery or used by the robotic system 115 to determine motions, actions, and operations of a robotic arm 120 or surgical instrument 125. Known techniques for creating virtual bone models can be utilized, such as those discussed in U.S. Pat. No. 9,675,461, titled "Deformable articulating templates" or U.S. Pat. No. 8,884,618, titled "Method of generating a patient-specific bone shell" both by Mohamed Rashwan Mahfouz, as well as other techniques known in the art.

The computing system 140 also communicates with a tracking system 165 that can be operated by the computing system 140 as a stand-alone unit. The surgical system 100 can utilize the Polaris optical tracking system from Northern Digital, Inc. of Waterloo, Ontario, Canada. The tracking system 165 can monitor a plurality of tracking elements, such as tracking elements 170, affixed to object of interest to track locations of multiple objects within the surgical field. The tracking system 165 functions to create a virtual three-dimensional coordinate system within the surgical field for tracking patient anatomy, surgical instruments, or portions of the robotic system 115. The tracking elements 170 can be tracking frames including multiple IR reflective tracking spheres, or similar optically tracked marker devices. In one example, the tracking elements are placed on or adjacent one or more bones of the patient 110. In other examples, the tracking elements 170 can be placed on a robot robotic arm 120, a surgical instrument 125, and/or an implant to accurately track positions within a virtual coordinate system. In each instance the tracking elements provide position data, such as patient position, bone position, joint position, robot robotic arm position, implant position, or the like.

The robotic system 115 can include various additional sensors and guide devices. For example, the robotic system 115 can include one or more force sensors, such as force sensor 180. The force sensor can provide additional force data or information to the computing system 140 of the robotic system 115. The force sensor 180 can be used to monitor impact or implantation forces during certain operations, such as insertion of an implant stem into a humeral canal. Monitoring forces can assist in preventing negative outcomes through force fitting components. In other examples, the force sensor 180 can provide information on soft-tissue tension in the tissues surrounding a target joint. In certain examples, the robotic system 115 can also include a laser pointer 185 that generates a laser beam or array that is used for alignment of implants during surgical procedures.

Figure 2:
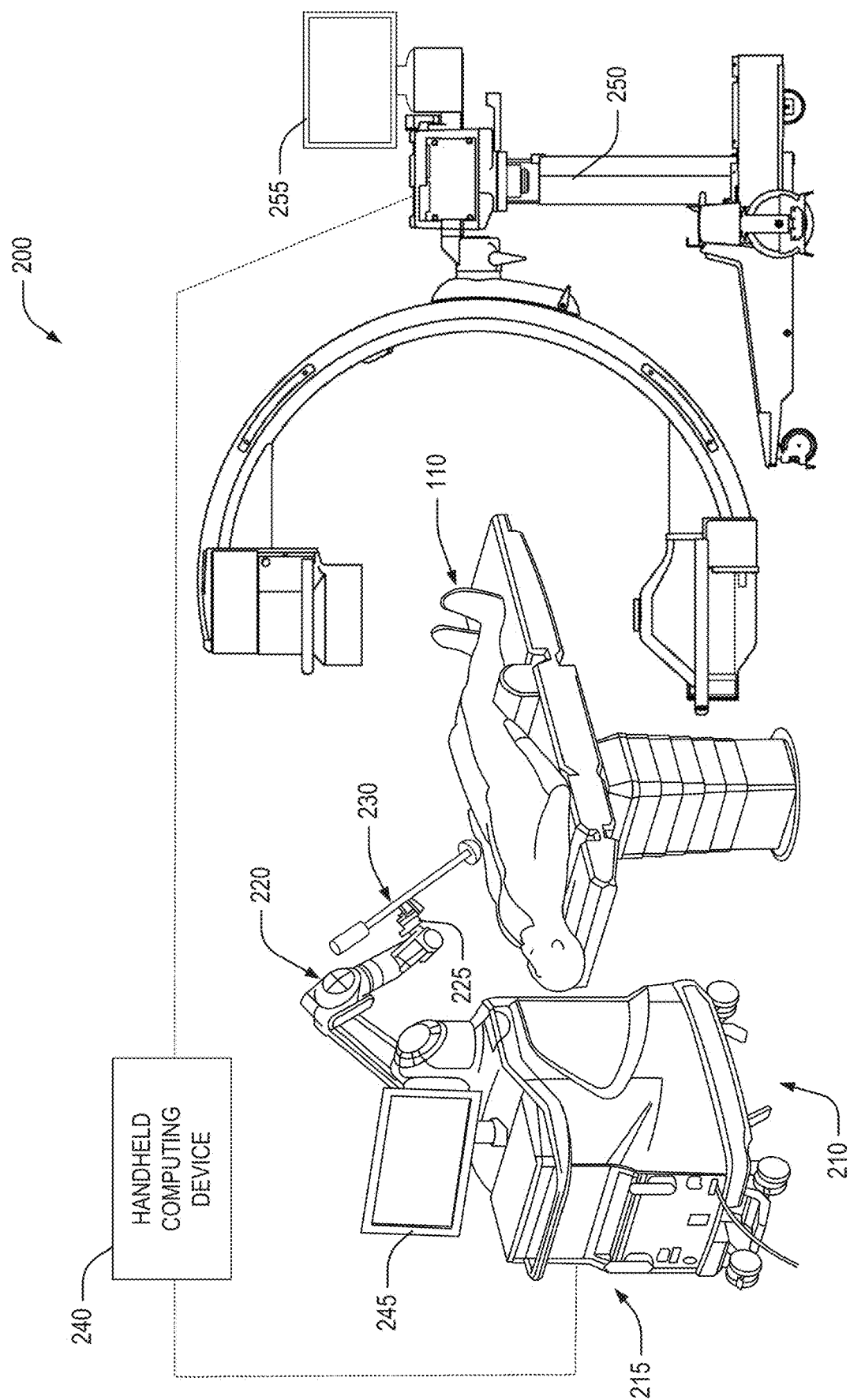
FIG. 2 is a diagrammatic view of a robotic surgical system including a C-arm fluoroscope according to the present disclosure.

The robotic system 115 is adapted in various manners to address the unique techniques discussed in this disclosure, the various adaptations are discussed in reference to robotic surgical system 200. FIG. 2 illustrates an example robotic surgical system 200 including robotic system 215 adapted for execution of the techniques discussed below. The robotic surgical system 200 includes a robotic system 215, a handheld computing device 240, and a C-arm fluoroscope 250. The robotic system 215 is capable of similar operations as the robotic system 115 discussed above and includes a computing system comparable to computing system 140 integrated into the robotic system 215 (referenced herein as the robotic control computer). The handheld computing device 240 executes as a user interface to robotic system 115 and also communicates with the C-arm 250. The handheld computing device 240 includes a wireless communication interface with the robotic control computer within the robotic system 215. The handheld computing device 240 can also wirelessly communicate with the C-arm 250 to obtain medical imaging, and in some examples control aspects of the C-arm 250. In certain examples, the handheld computing device 240 uses an integrated camera to obtain imaging directly from the screen of the C-arm 250.

In this example, the robotic system 215 can include computing system 140, robotic arm 220, end effector 225, impaction instrument 230, and display screen 245. The robotic system 215 can operate in multiple modes including fully automatic and cooperative modes. In a cooperative mode the surgeon can directly manipulate the position of the end effector 225 to position the impaction instrument 230 as needed during the surgical procedure. The robotic arm 220 can limit movement in cooperative mode to avoid sensitive areas or maintain certain planned surgical parameters as discussed in greater detail below. In an example, the robotic arm 220 maintains a position selected by the surgeon and controls inclination and anteversion in accordance with a pre-operative plan and intra-operative measurements.

Within the acetabular shell implant procedure discussed below, the C-arm 250 can be used to provide intra-operative imaging that enables precise placement of the acetabular shell with the robotic system 215, but without any additional external navigation equipment, such as an optical navigation system. During the procedure, the handheld computing device 240 obtains multiple images from the C-arm 250 to analyze position of the anatomy and various positions of the impaction instrument 230 holding an acetabular shell. Based on analysis of the various medical images obtained from the C-arm 250, the system can accurately position the acetabular shell on the impaction instrument 230 using the robotic arm 220. Once positioned, the surgeon can impact the acetabular shell into the acetabulum while position and orientation are maintained by the robotic arm 220.

In some examples, the handheld computing device 240 operates merely as a user interface and data collection device, while all analysis and other operations are performed on the computing system 140 within the robotic system 215. In other examples, the handheld computing device 240 can perform operations to support the user interface, data collection, and analysis tasks, while merely sending robot control commands to the computing device 140 within the robotic system 215. In the data collection mode, the handheld computing device 240 obtains medical images from the C-arm 250. In some examples, the medical images can be obtained over a wired or wireless network connection with the C-arm 250. In other examples, the handheld computing device 240 can utilize an integrated camera to capture medical images directly from a display screen 255 on the C-arm 250. In certain examples, all computing functions can be performed by the computing system 140 integrated into the robotic system 215—in these examples the handheld computing device 240 is not used.

Figure 3:
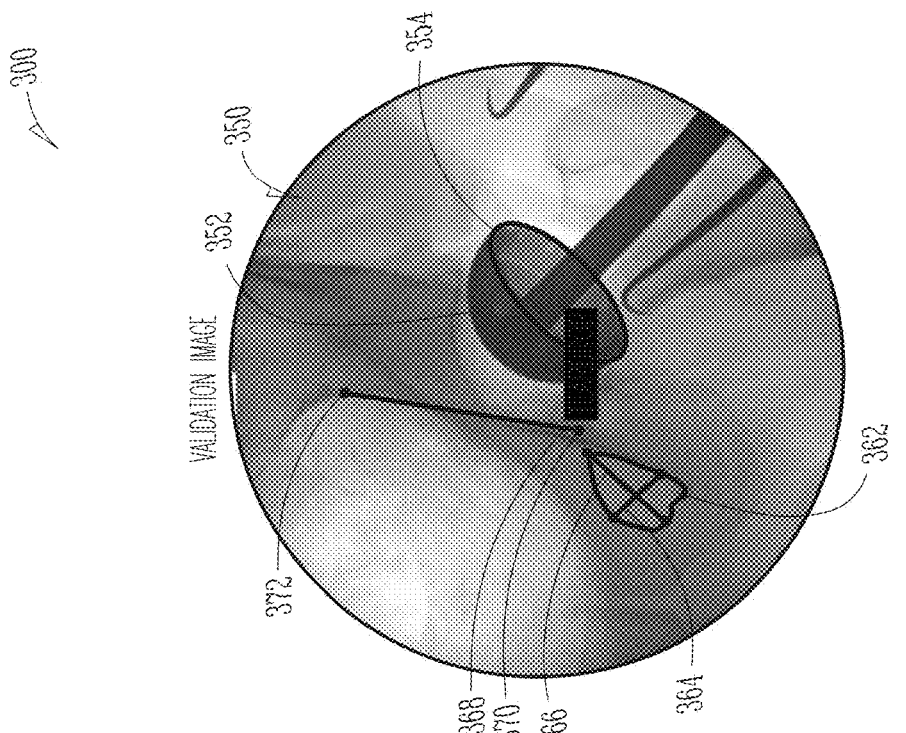
FIG. 3 illustrates a graphical user interface enabling image registration based on anatomical landmarks according to the present disclosure.
Figure 3:
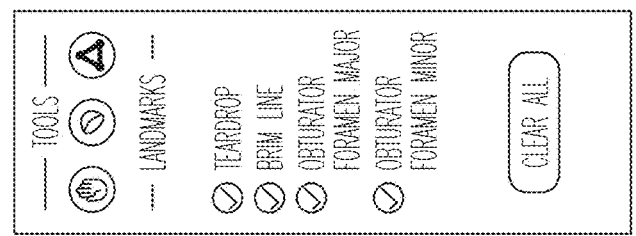
Figure 3:
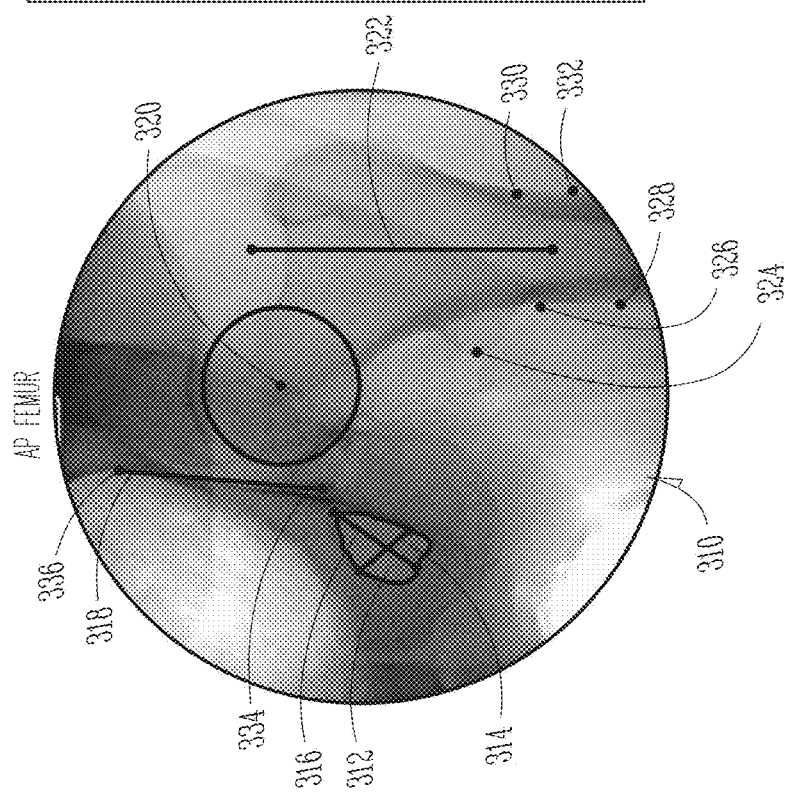

FIG. 3 illustrates a graphical user interface 300 enabling image registration based on anatomical landmarks according to the present disclosure. One important aspect of the present disclosure is the ability to register (e.g., align) images taken of the patient's anatomy over the course of the procedure. The example interface 300 depicts various anatomical landmarks used during the image registration process. The interface 300 includes an anterior-posterior (AP) femur reference image 310 and a validation image 350. The validation image 350 could be any of the various images taken throughout the procedures discussed herein.

In this example, the AP femur image 310 illustrates a variety of landmarks including an obturator foramen 312, a brim line 318, a femoral head center 320, and a femoral axis 322. The obturator foramen 312 can include an obturator foramen minor axis 314 and an obturator foramen major axis 316. In some examples, the outline of the obturator foramen 312 is also used to assist with registration, as the outline contour should be consistent throughout the various images.

Additional landmarks included on the AP femur image 310 include a lesser trochanter 324, shaft medial points 326, 328, and shaft lateral points 330, 332. In some examples, the femoral axis 322 is calculated from the shaft medial points 326, 328 and the shaft lateral points 330, 332. In this example, the brim line 318 includes a teardrop point 334 and an anterior pelvic brim point 336, with the brim line 318 tangential to the pelvic brim between these points.

The validation image 350 illustrates a similar set of landmarks including an obturator foramen 362, an obturator minor axis 364, an obturator major axis 366, and a brim line 368. The validation image 350 also includes an acetabular shell 352 and an elliptical outline 354 that outlines the opening of the acetabular shell 352. As discussed in detail below, the elliptical outline 354 is key to determining coordinate alignment between the anatomical images, the patient's anatomy, and the robotic system—once the coordinates are in alignment the robotic system 215 can be used to accurately position the acetabular shell in the patient's acetabulum for impaction.

The brim line 368 in the validation image 350 is created by connecting a teardrop point 370 with an anterior pelvic brim point 372 tangential to the pelvic brim. Similar to the obturator foramen, the brim line 368 is a key landmark in aligning/registering images to one another as this line should remain consistent between images (assuming a stationary patient and imaging source). The image registration process, discussed in reference to FIG. 7, involves matching obturator foramen outlines (contours) and brim lines to calculate image rotation and scaling, with the teardrop point used for residual translation. The image registration process can use an iterative closest point algorithm to match the various landmarks.

Figure 4A:
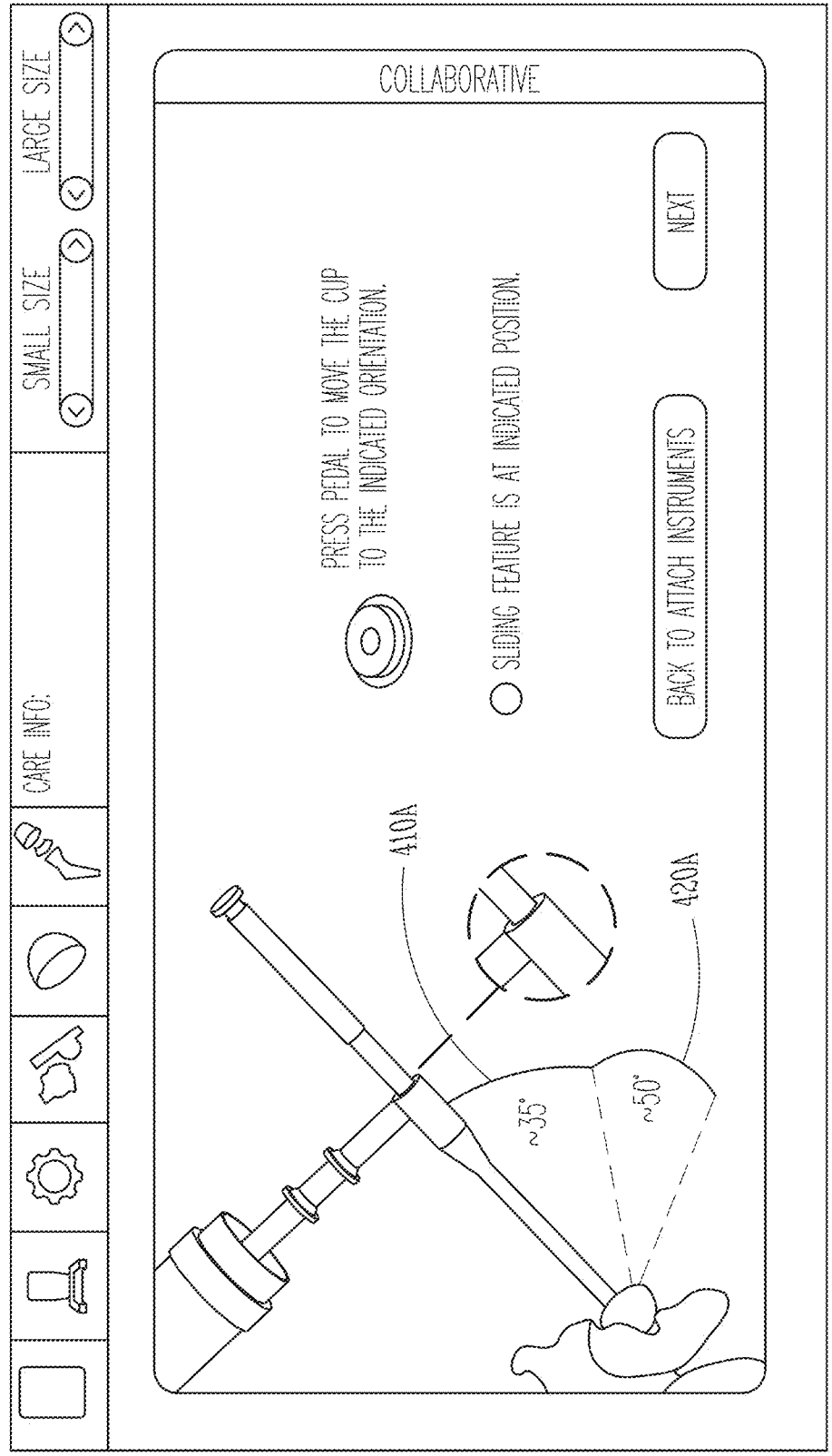
FIGS. 4A and 4B illustrate graphical user interfaces depicting a portion of the procedure to align coordinates between the robotic system and the patient according to the present disclosure.
Figure 4B:
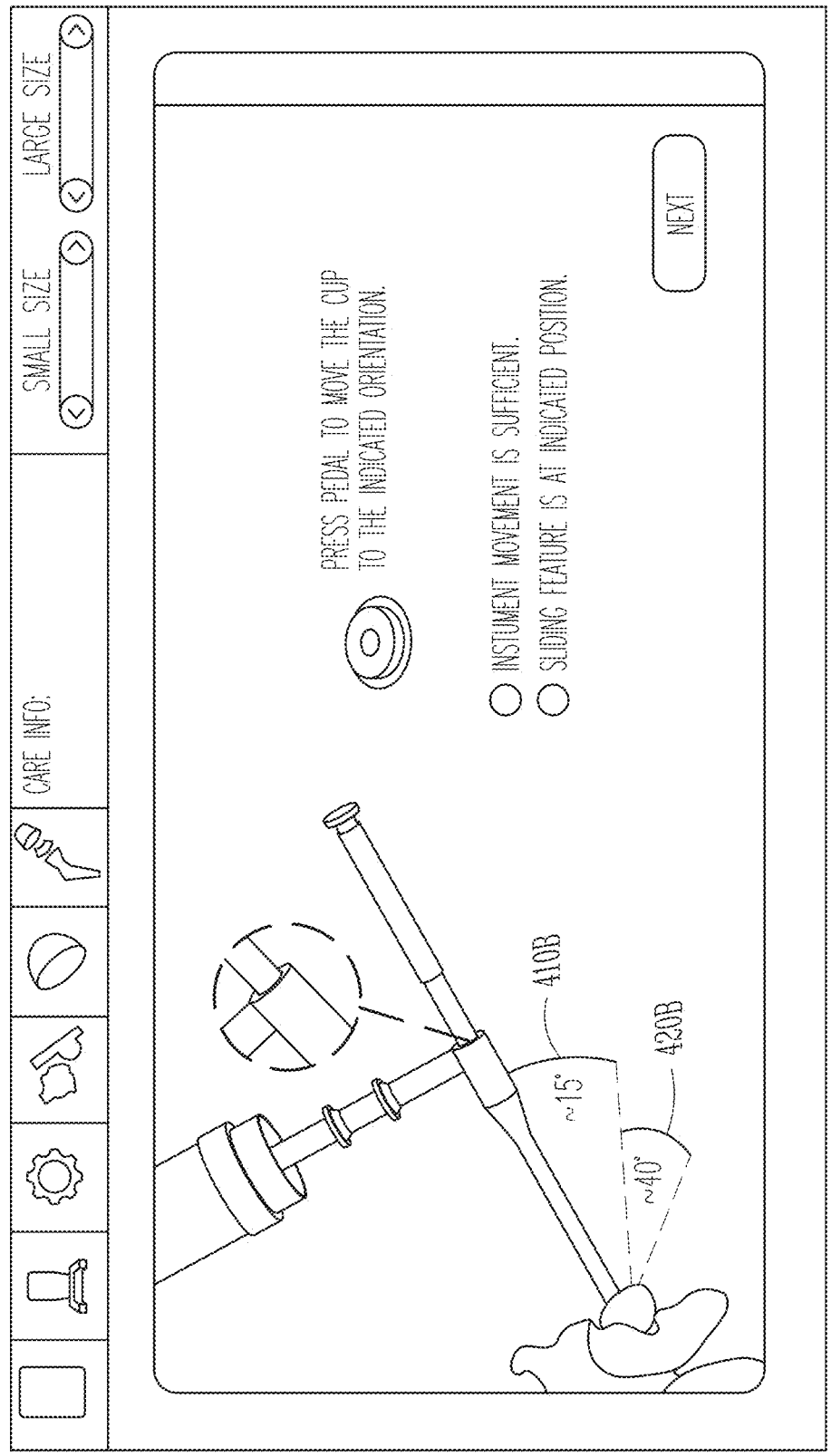

FIGS. 4A and 4B illustrate graphical user interfaces 400A, 400B depicting a portion of the procedure to align coordinates between the robotic system and the patient according to the present disclosure. A key portion of the procedure discussed herein involves capturing fluoroscopic images including the impaction instrument and acetabular shell in two different inclination and anteversion orientations within the patient's acetabulum. User interface 400A illustrates a user interface screen instructing a surgeon to position the impaction instrument attached to the robotic arm 220 in approximately 50 degrees of inclination 420A and 35 degrees of anteversion 410A. Once in the instructed position, a calibration image is captured for analysis as discussed below in the various techniques. Note, the use of the term "calibration image" is merely a label or reference for a first image in the intra-operative technique described herein. As is common in THA procedures, inclination is considered a positive angular displacement measured in the coronal (frontal) plane in reference to a proximo-distal axis of the pelvis, while anteversion is a negative angular displacement measured as an angle between the acetabular axis and the frontal plane. The purposes of this disclosure, inclination and anteversion are further defined below.

User interface 400B illustrates a user interface screen instructing a surgeon (or operator) to position the impaction instrument 230 attached to the robotic arm 220 in approximately 40 degrees of inclination 420B and 15 degrees of anteversion 410B. Once in the second instructed position, a navigation image is captured for analysis as discussed below. The instructed inclination and anteversion values result in large enough positional changes of the elliptical outline of the acetabular shell in fluoroscopic images to enable calculations to align coordinate systems needed to accurately position the acetabular shell with the robotic system 215 without use of external navigation systems.

Figure 5:
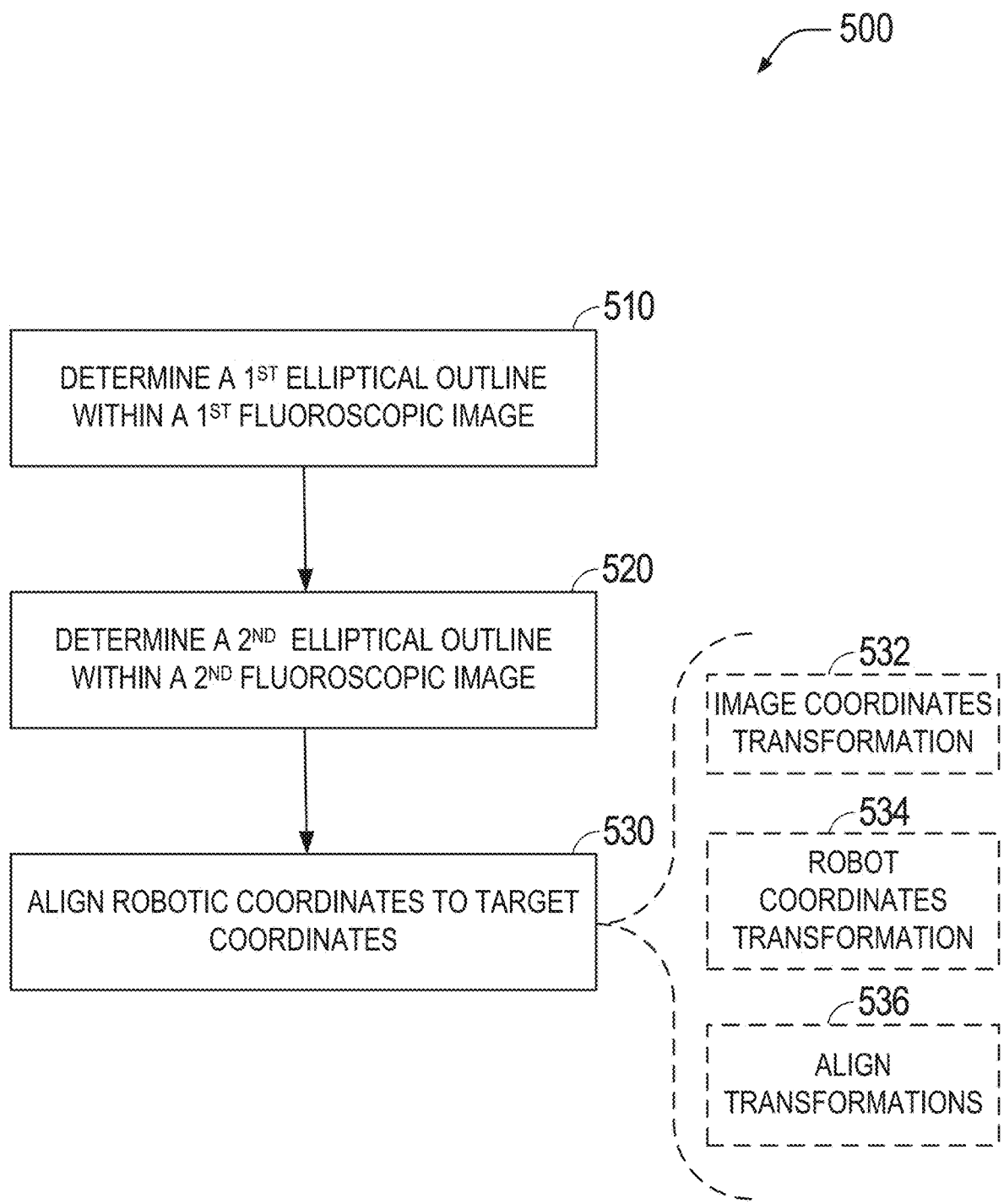
FIG. 5 is a flowchart illustrating a technique for coordinate alignment according to the present disclosure.

FIG. 5 is a flowchart illustrating a technique 500 for coordinate alignment according to the present disclosure. The technique 500 covers the basics of aligning the coordinates for the robotic system 215 with image and/or patient coordinates (e.g., target coordinates). The technique 500 can include operations for determining a first elliptical outline at 510, determining a second elliptical outline at 520, and aligning the robotic coordinates to the target coordinates at 530. In an example, the technique 500 can be performed on the handheld computing device 240 with images obtained from the C-arm 250. In another example, the technique 500 is performed within the robotic system 215 on a computing device 140 integrated into the robotic system 215. In this example, the images may be obtained directly from the C-arm 250 or via the handheld computing device 240 and transferred to the robotic system 215. In any example, the robotic system 215 is involved in positioning the robotic arm 220 and impaction instrument 230 in cooperation with the surgeon (or operator).

The technique 500 begins at 510 with the computing device determining a first elliptical outline within a first fluoroscopic image of the patient's acetabulum with the acetabular shell (e.g., cup-shaped implant) positioned in a calibration position. As shown in FIG. 4A, the calibration position can be with the acetabular shell positioned at approximately 50 degrees of inclination and 35 degrees of anteversion. Calculation of the first elliptical outline of the acetabular shell allows for further calculation of inclination and anteversion in the calibration orientation.

In an example, acetabular shell angle can be determined from the first elliptical outline based on the following algorithm. The characteristics of the ellipse are used to determine the three-dimensional (3D) orientation of the hemisphere of the acetabular shell. This 3D orientation corresponds to the orientation of the acetabular axis which allows the computation of the inclination and anteversion angles. The angle of the shell axis is calculated in 3 steps:
1) The ellipse is projected on a virtual plane normal to the vector from the source to the center of the ellipse
2) The projected ellipse's axes are used to calculate the angle between the virtual plane and the hemisphere using the equation $\theta'=\cos^{-1}(IJ/I_0J_0)$ where IJ is the long axis of the ellipse and $I_0J_0$ is the short axis of the ellipse
3) The final angle is then $\theta=\theta'+\alpha$ where $\alpha$ is the angle between the virtual plane and the image plane The angle of the virtual plane is calculated with the following: $\alpha=\tan^{-1}(HP/OH)$ where HP is the distance from the center of the ellipse to the projection of the source on the image plane and OH is the distance between the source and the projection of the source on the image plane.

Once the orientation of the cup relative to the image has been determined, it needs to be converted in terms of inclination and anteversion angles in the patient's coordinate system. In an example, the technique discussed herein uses radiographic angles, defined as follows:
The anteversion angle is the angle between the acetabular axis and the frontal plane.
The inclination angle is the angle between the sagittal plane and the projection of the acetabular axis on the frontal plane In this example, the algorithm assumes that the image plane is parallel to the frontal plane and that the Sagittal plane is normal to the Medio-lateral axis of the patient (which is transferred from the full AP pelvis image assuming no rotation of the C-arm or patient). The algorithm then makes the following assumptions to distinguish between multiple possible solutions:
The dome of the cup can only point towards the head of the patient when it is inserted into the acetabulum. In other words, the inclination angle must be between −90 and +90 degrees.
The cup is in anteversion, i.e. the version angle must be positive. Therefore, the version angle must be between 0 and +90 degrees.

At 520, the technique 500 continues with the computing device determining a second elliptical outline within a second fluoroscopic image of the patient's acetabulum with the acetabular shell positioned in a navigation position (see FIG. 4B). The second elliptical outline is computed in a manner similar to the first elliptical outline. At 530, the technique 500 concludes with the computing device aligning the robotic coordinate system with the target coordinate system. In an example, operation 530 can include the computing device performing intermediate operations such as image coordinate transformation at 532, robot coordinates transformation at 534, and alignment of transformations at 536. At 532, the computing device computes a transformation between the first elliptical outline in the calibration image and the second elliptical outline in the navigation image in the image coordinate system. At 534, the computing device computes a transformation between the known position and orientation of the acetabular shell (affixed to the end of the impaction instrument 230 held by the robotic arm 220) in the calibration position and the known position and orientation of the acetabular shell in the navigation position in robot coordinates. Finally, at 536, the technique 500 includes the computing device aligning the image coordinate transformation from operation 532 with the robot coordinate transformation from operation 534. The technique 500 outputs a transformation to align robotic coordinates to the target coordinates. In this example, the technique 500 calculates the transformation in rotation (e.g., orientation of the instrument) and allows the surgeon to guide actual position of the acetabular shell. In this example, the robotic arm 220 moves to a target orientation, while maintaining a fixed center of rotation of the acetabular shell. In other examples, the output of technique 500 can allow for the robotic system 215 to be commanded to position an acetabular shell within a patient's acetabulum at a precise inclination and anteversion, based on imaging of the patient's acetabulum.

Figure 6:
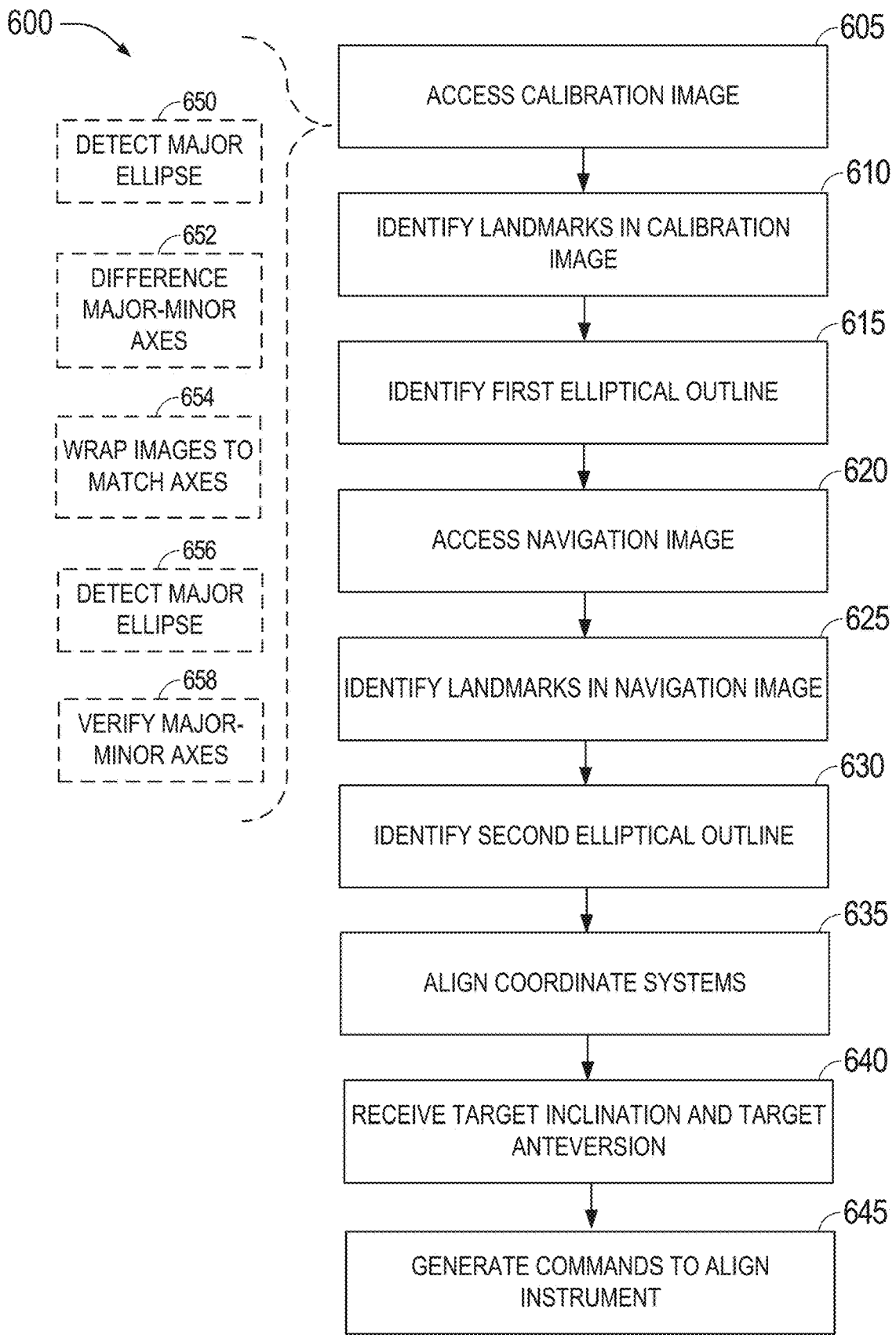
FIG. 6 is a flowchart illustrating a technique for robotically assisted implant positioning according to the present disclosure.

FIG. 6 is a flowchart illustrating a technique 600 for robotically assisted implant positioning according to the present disclosure. In this example, the technique 600 can include operations such as accessing a calibration image at 605, identifying landmarks in the calibration image at 610, identifying a first elliptical outline at 615, accessing a navigation image at 620, identifying landmarks in the navigation image at 625, identifying a second elliptical outline at 630, aligning coordinate systems at 635, receiving target inclination and anteversion parameters at 640, and generating commands to align instrument at 645. As with other techniques discussed herein, technique 600 can be performed on any of the computing devices discussed in association with the robotic surgical system 200. For example purposes, the technique 600 is discussed here as operating on the handheld computing device 240.

In this example, the technique 600 begins at 605 with the handheld computing device 240 accessing a calibration image from the C-arm 250. The handheld computing device 240 can access images from the C-arm 250 over a network connection to the C-arm 250 or using an integrated camera and taking a picture of the calibration image on the display 255 on the C-arm 250. In examples using the integrated camera, the technique 600 includes a series of sub-operations to correct for any misalignment between the handheld computing device 240 and the display screen 255 of the C-arm 250 during image capture. In this example, the C-arm image is discussed as an ellipse, but the system can handle any known detector shape, such as a circle, square, squircle, or other known detector shapes. Accordingly, at 650, the technique 600 can continue with the handheld computing device 240 detecting the largest ellipse in the captured image (note, fluoroscopic C-arm's generate round images). At 652, the technique 600 continues with the handheld computing device 240 detecting the difference between the major axis and the minor axis of the largest ellipse. In other examples, at 652, the handheld computing device 240 can utilize other image features, such as corners of a square or squircle to make the image adjustment. At 654, the technique 600 continues with the handheld computing device 240 warping the captured C-arm image so that the minor axis is equal to the major axis. In other examples, at 654, the handheld computing device 240 can warp the C-arm image to reproduce the known detector shape by using a homographic transform. At 656, the technique 600 continues with the handheld computing device 240 detecting the largest ellipse in the warped image and then at 658 verifying that the major axis is equal to the minor axis in the largest ellipse in the warped image. In some examples, the verification operations 656 and 658 may not be performed as the image transform is known and the output certain.

Once the captured image is corrected for any misalignment, the technique 600 continues at 610 with the handheld computing device 240 identifying landmarks in the calibration image. In some examples, initial identification of the landmarks can be performed automatically by the computing device, such as handheld computing device 240. In these examples, the handheld computing device 240 can then present the landmarked image within a user interface (see example in FIG. 3) and allow the surgeon to adjust the landmarks as needed. Automatic landmark identification can utilize various image processing techniques including machine learning models trained on known input images. In certain examples, the system 200 uses a semi-automatic landmarking technique on subsequent images after a user (e.g., surgeon) manually places landmarks on an initial image (e.g., reference image). For example, after manually landmarking a reference image a user can place a series of points on an anatomical structure (e.g., teardrop landmark for the pelvis) and the system can use the relative position and surrounding image data of each point on the reference image to initialize the corresponding points on the subsequent image. In other examples, at 615 the handheld computing device 240 presents a user interface for the surgeon to landmark the calibration image manually. Landmarks can include those discussed above in reference to FIG. 3. In an example, manual landmarking will request identification of at least a teardrop point, a brim line between the teardrop and a point on the anterior pelvic brim, the obturator foramen major axis, and the obturator foramen minor axis.

Once landmarking is completed on the calibration image, the technique 600 continues at 615 with the handheld computing device 240 identifying a first elliptical outline of the acetabular shell within the calibration image. In an example, the elliptical outline of the acetabular shell can be identified within the image using a Hough transform to detect the circular contour representing the acetabular shell (cup) in the fluoroscopic image. More specifically, the Hough transform is used to identify a region-of-interest containing an elliptical outline. Identification of the elliptical outline then proceeds using a LO-RANSAC algorithm (locally optimized random sample consensus) 3D plane fitting algorithm to find the optimal circular contour of the shell. The vertices of the shell are then identified to set the ellipse inclination by analyzing the distance of each point to the cup center. The vertices of the shell represent points on the outline that define the ellipse's major axis. Once inclination of the shell is defined, based on the expected laterality, a circle is fitted on the lower portion of the ellipse. The portion of the fitted circle that is comprised between both previously computed vertices is used in a series of optimizers to perform adjustments on the center, the length of the minor axis, and the inclination of the major axis. After the handheld computing device 240 generates a proposed outline identifying the elliptical opening of the acetabular shell, a user interface is presented to allow for manual adjustment of the ellipse.

Once the first elliptical outline is identified the technique 600 continues at 620 with the handheld computing device

240 accessing a navigation image. The navigation image is generated with the robotic arm 220, impaction instrument 230 and acetabular shell adjusted to a second orientation, such as an approximate inclination of 40 degrees and anteversion of 15 degrees. Note, the two different inclination and anteversion orientations used for collection of the calibration image and the navigation image are somewhat arbitrary, what is important for the technique 600 is that the two orientations used are significantly different (e.g., sufficiently different for detection of different acetabular axes). In practice, testing has indicated that 10 degrees of variation in either inclination or anteversion (or a combination of the two) is sufficient to obtain the needed measurements. In an example, the following formula captures the required variation in orientations:

$$\sqrt{(incl.variation)^2 + (ant.variation)^2} \geq 10 \text{ degrees}$$

The process of accessing the navigation image is similar to that described above for the calibration image. At 625, the technique 600 continues with the handheld computing device 240 landmarking the navigation image or providing an interface to manually landmark-again landmarking the navigation image involves similar operations to landmarking the calibration image described above. At 630, the technique 600 continues with the handheld computing device 240 identifying a second elliptical outline of the acetabular shell within the navigation image. Identification of the second elliptical outline is done by the handheld computing device 240 using operations similar to those discussed above in reference to identifying the first elliptical outline at 615.

At 635, the technique 600 continues with the handheld computing device 240 aligning coordinate systems between the robotic system 215 and the C-arm 250 (and/or patient anatomy). The computer operations performed to align coordinate systems are discussed in detail above in reference to technique 500. The technique 600 continues at 640 with the handheld computing device 240 receiving target implantation parameters for inclination and anteversion. The target implantation parameters can be accessed from a pre-operative plan or input intra-operatively within a user interface generated on the handheld computing device 240. Even in examples using a pre-operative plan, intra-operative adjustments can be made to the target inclination and anteversion on the handheld computing device 240.

Finally, at 645, the technique 600 can conclude with the handheld computing device 240 generating commands for the robotic system 215. The commands generated at 645 instruct the robotic system 215 to move the robotic arm 220 and impaction instrument 230 to align the acetabular shell in the patient's acetabulum for impaction at the target implantation parameters.

Figure 7:
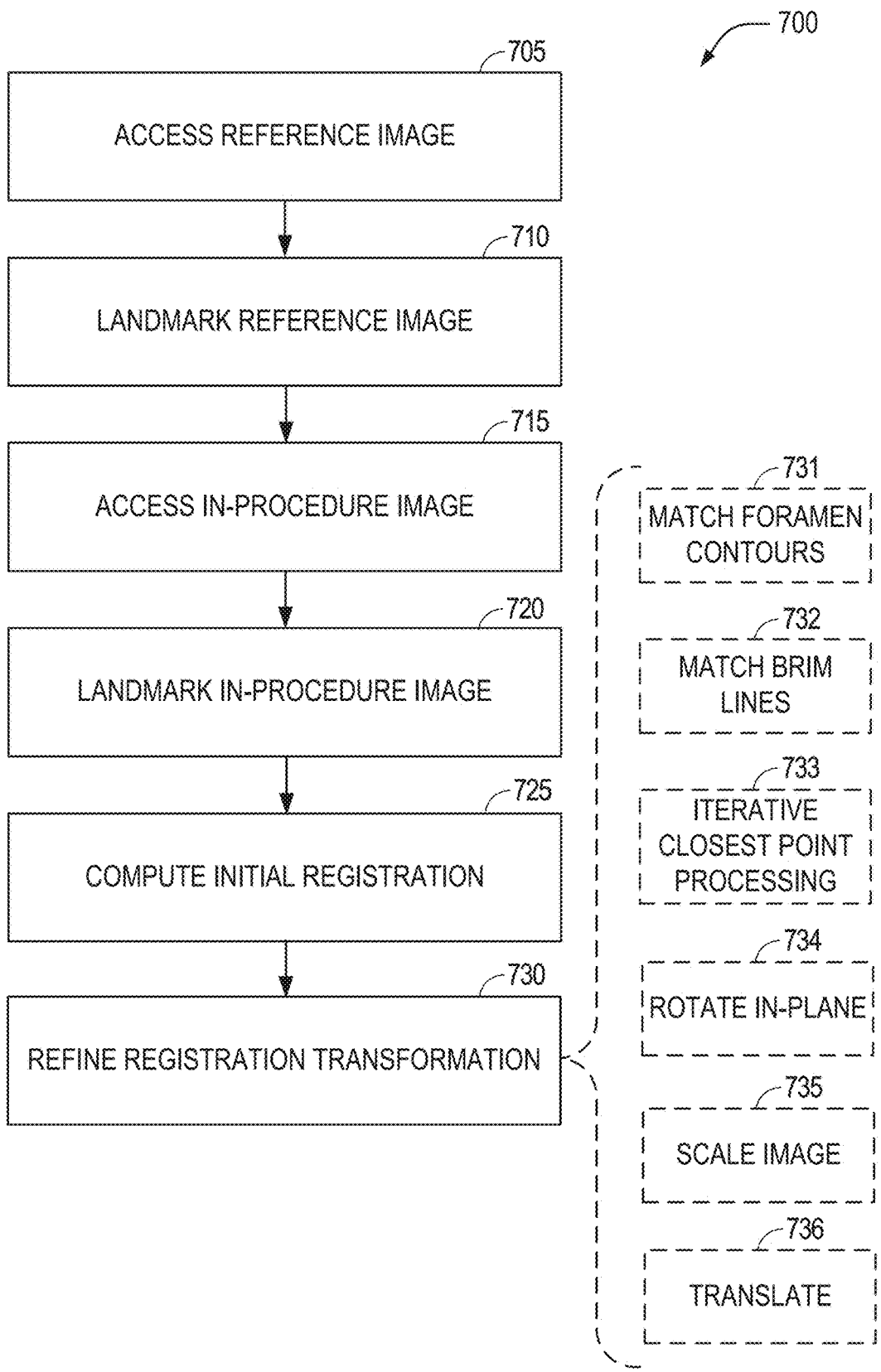
FIG. 7 is a flowchart illustrating a technique for image registration according to the present disclosure

FIG. 7 is a flowchart illustrating a technique 700 for image registration according to the present disclosure. The technique 700 outlines a generic procedure for registering two images of the same anatomical structure taken at different points in a surgical procedure. The reference image and in-procedure image are merely convenient labels attached to the two images in discussion of this technique, in practice a reference image, such as the AP Femur image discussed above is captured and in-procedure images could be the calibration or navigation images discussed herein (among others). The technique 700 is discussed below in reference to a computing device performing the various operations, in various examples the computing device can be the handheld computing device 240 or computing system 140 integrated into robotic system 215.

In this example, the technique 700 begin at 705 with the computing device accessing a reference image captured of the patient anatomy using the C-arm 250. Accessing the reference image can involve accessing the image file from the C-arm over a network connection or capturing the reference image from display 255 using a camera within the computing device. At 710, the technique 700 continues with the computing device landmarking the reference image. Anatomical landmarks are identified on the reference image in the various manner discussed within this disclosure. Landmarks identified include at least obturator foramen contour (outline), and a brim line.

At 715, the technique 700 continues with the computing device accessing an in-procedure image captured on the C-arm 250. The technique 700 continues at 720 with the computing device landmarking the in-procedure image with the same landmarks as identified on the reference image. At 725, the technique 700 continues with the computing device computing an initial registration between the reference image and the in-procedure image based on the identified landmarks. The initial registration can include calculation of an angle between brim lines as well as an angle between lines running from a teardrop point to a barycenter of foramen axes. The calculated angles are then averaged to generate an initial transformation between images. At 730, the technique 700 concludes with the computing device refining registration transformation through various additional operations.

The additional operations can include matching obturator foramen contours at 731, matching brim lines at 732, performing iterative closest point processing at 733, calculating in-place rotation at 734, scaling the image at 735, and calculating a translation at 736. The iterative closest point processing at 733 is utilized to calculate the best match between landmarks such as the obturator foramen contours (outlines) and brim lines in each image. The results of the iterative closest point processing are used at 734 to refine in-plane rotation transformation and for scaling transformation at 735. Translation at 736 can be done through determining a distance between teardrop points in the images (after application of rotation and scaling).

Figure 8:
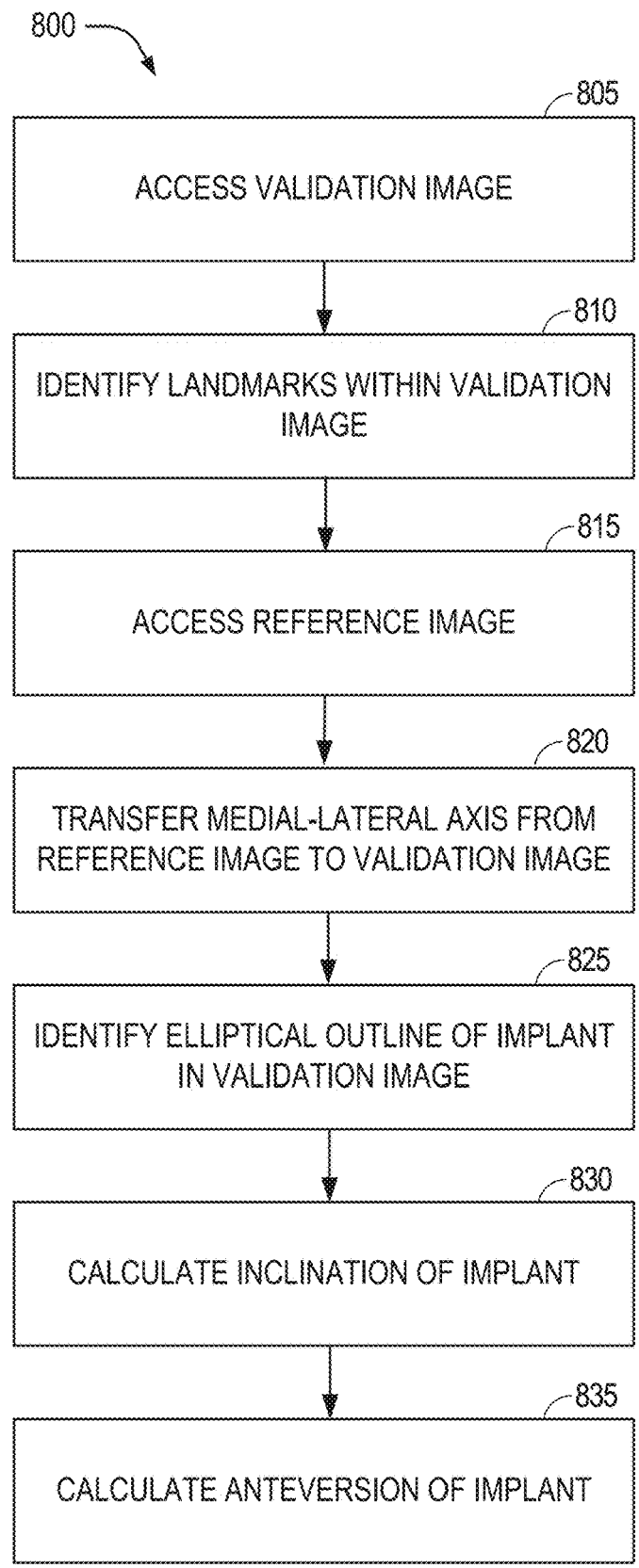
FIG. 8 is a flowchart illustrating a technique for implant position and orientation validation according to the present disclosure.

FIG. 8 is a flowchart illustrating a technique 800 for implant orientation validation according to the present disclosure. Technique 800 focuses on a procedure for validating orientation of the impacted acetabular shell (e.g., inclination and anteversion).

In this example, the technique 800 begins at 805 with the computing device accessing a validation image captured by the C-arm 250. At 810, the technique 800 continues with the computing device identifying landmarks within the validation image in one of the various manners discussed within this disclosure. Once the validation image is landmarked, the technique 800 continues at 815 with the computing device accessing a reference image, such as an AP pelvis image captured by the C-arm 250. The accessed reference image includes landmarks identified earlier in the procedure including a medial-lateral (ML) axis of the pelvis. At 820, the technique 800 continues with the computing device transferring the ML axis from the reference image to the validation image based on an assumption that the C-arm and patient have not rotated (e.g., moved). Alternatively, the ML axis could be transferred based on landmarks common across both images. For example, the validation image will include operative side landmarks such as a brim line and the obturator foramen that will also be visible in the reference image. Matching positions of the common landmarks allows for transfer of the ML axis into the validation image.

At 825, the technique 800 continues with the computing device identifying the elliptical outline of the implant (e.g., acetabular shell) within the validation image. Identification of the elliptical outline is performed in a manner similar to that described above. At 830, the technique 800 continues with the computing device calculating inclination of the implant based on the elliptical outline and the transferred ML axis. Finally, at 835, the technique 800 can conclude with the computing device calculating the anteversion of the implant based on the elliptical outline and the transferred ML axis. The inclination and anteversion of the implant (e.g., acetabular shell) are calculated as described above in reference to FIG. 6.

Figure 9:
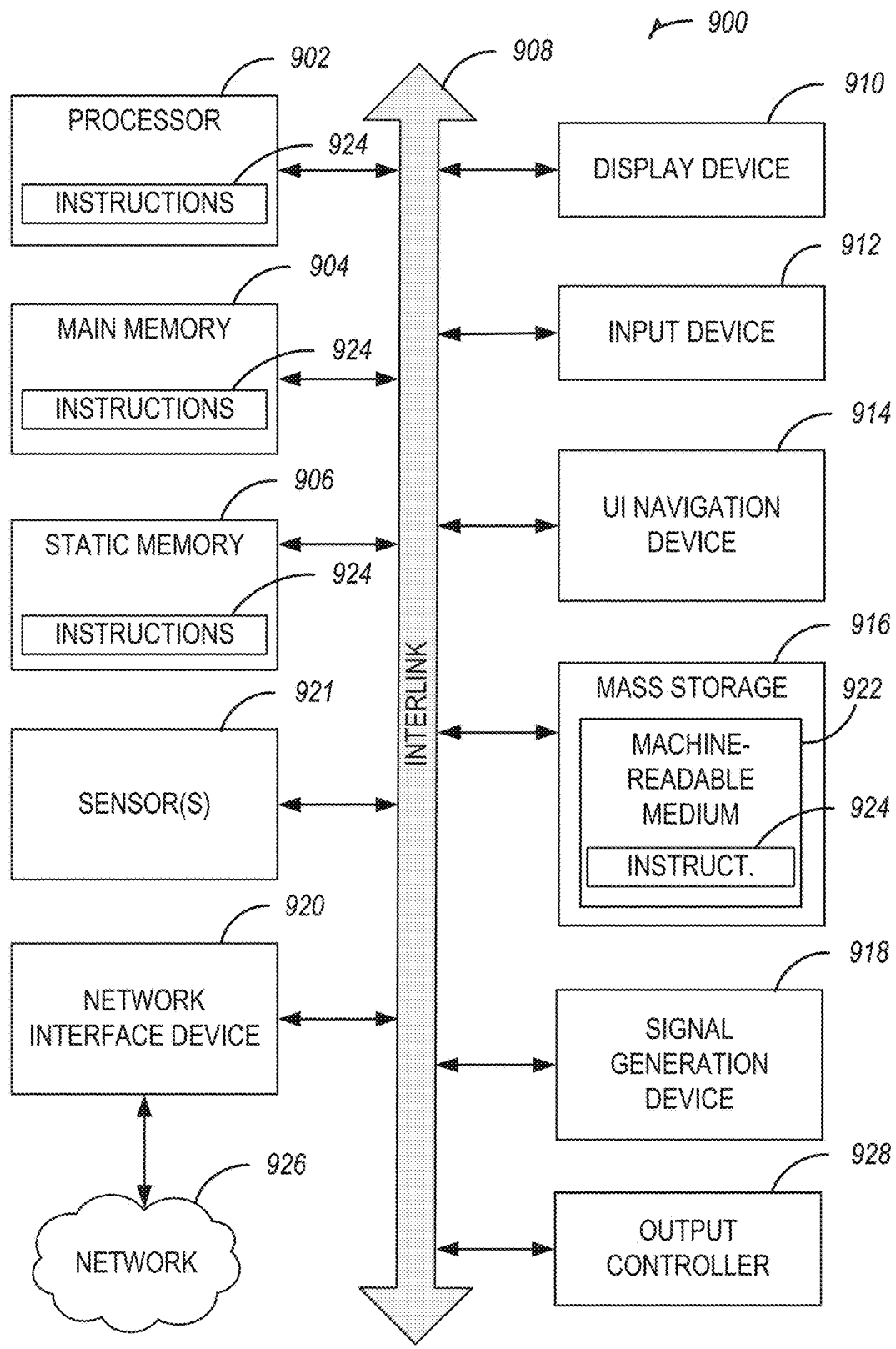
FIG. 9 illustrates a block diagram of an example machine upon which any one or more of the techniques discussed herein may be performed in accordance with some embodiments.

FIG. 9 illustrates a block diagram of an example machine 900 upon which any one or more of the techniques discussed herein may be performed in accordance with some embodiments. For example, machine 900 can comprise computing system 140 of FIG. 1 or handheld computing device 240 of FIG. 2. Machine 900 can comprise an example of a controller for robotic system 115 or 215 and sensors 921 can include tracking elements 90. As such instructions 924 can be executed by processor 902 to generate and correlate position and orientation information to determine the position and orientation of a surgical instrument coupled to the robotic arm via a quick connect and relative to robotic arm 120, 220 and/or impaction instrument 230.

In alternative embodiments, machine 900 may operate as a standalone device or may be connected (e.g., networked) to other machines. In a networked deployment, machine 900 may operate in the capacity of a server machine, a client machine, or both in server-client network environments. In an example, machine 900 may act as a peer machine in peer-to-peer (P2P) (or other distributed) network environment. Machine 900 may be a personal computer (PC), a tablet PC, a set-top box (STB), a personal digital assistant (PDA), a mobile telephone, a web appliance, a network router, switch or bridge, or any machine capable of executing instructions (sequential or otherwise) that specify actions to be taken by that machine. Further, while only a single machine is illustrated, the term "machine" shall also be taken to include any collection of machines that individually or jointly execute a set (or multiple sets) of instructions to perform any one or more of the methodologies discussed herein, such as cloud computing, software as a service (SaaS), other computer cluster configurations.

Machine (e.g., computer system) 900 may include hardware processor 902 (e.g., a central processing unit (CPU), a graphics processing unit (GPU), a hardware processor core, or any combination thereof), main memory 904 and static memory 906, some or all of which may communicate with each other via interlink (e.g., bus) 908. Machine 900 may further include display unit 910, alphanumeric input device 912 (e.g., a keyboard), and user interface (UI) navigation device 914 (e.g., a mouse). In an example, display unit 910, input device 912 and UI navigation device 914 may be a touch screen display. Machine 900 may additionally include storage device (e.g., drive unit) 916, signal generation device 918 (e.g., a speaker), network interface device 920, and one or more sensors 921, such as a global positioning system (GPS) sensor, compass, accelerometer, or other sensors. Machine 900 may include output controller 928, such as a serial (e.g., Universal Serial Bus (USB), parallel, or other wired or wireless (e.g., infrared (IR), near field communication (NFC), etc.) connection to communicate or control one or more peripheral devices (e.g., a printer, card reader, etc.).

Storage device 916 may include machine readable medium 922 on which is stored one or more sets of data structures or instructions 924 (e.g., software) embodying or utilized by any one or more of the techniques or functions described herein. Instructions 924 may also reside, completely or at least partially, within main memory 904, within static memory 906, or within hardware processor 902 during execution thereof by machine 900. In an example, one or any combination of hardware processor 902, main memory 904, static memory 906, or storage device 916 may constitute machine readable media.

While machine readable medium 922 is illustrated as a single medium, the term "machine readable medium" may include a single medium or multiple media (e.g., a centralized or distributed database, and/or associated caches and servers) configured to store the one or more instructions 924. The term "machine readable medium" may include any medium that is capable of storing, encoding, or carrying instructions for execution by machine 900 and that cause machine 900 to perform any one or more of the techniques of the present disclosure, or that is capable of storing, encoding or carrying data structures used by or associated with such instructions. Non-limiting machine readable medium examples may include solid-state memories, and optical and magnetic media.

Instructions 924 may further be transmitted or received over communications network 926 using a transmission medium via network interface device 920 utilizing any one of a number of transfer protocols (e.g., frame relay, internet protocol (IP), transmission control protocol (TCP), user datagram protocol (UDP), hypertext transfer protocol (HTTP), etc.). Example communication networks may include a local area network (LAN), a wide area network (WAN), a packet data network (e.g., the Internet), mobile telephone networks (e.g., cellular networks), Plain Old Telephone (POTS) networks, and wireless data networks (e.g., Institute of Electrical and Electronics Engineers (IEEE) 902.11 family of standards known as Wi-Fi®, IEEE 902.16 family of standards known as WiMax®), IEEE 902.15.4 family of standards, peer-to-peer (P2P) networks, among others. In an example, network interface device 920 may include one or more physical jacks (e.g., Ethernet, coaxial, or phone jacks) or one or more antennas to connect to communications network 926. In an example, network interface device 920 may include a plurality of antennas to wirelessly communicate using at least one of single-input multiple-output (SIMO), multiple-input multiple-output (MIMO), or multiple-input single-output (MISO) techniques. The term "transmission medium" shall be taken to include any intangible medium that is capable of storing, encoding or carrying instructions for execution by machine 900, and includes digital or analog communications signals or other intangible medium to facilitate communication of such software.

The systems, devices and methods discussed in the present application can be useful in performing robotic-assisted surgical procedures that utilize robotic surgical arms that can be used to position devices relative to a patient to perform arthroplasty procedures, such as total hip arthroplasties. In particular, the systems, devices and methods disclosed herein are useful in improving the accuracy with which cup-shaped implants are implanted, such as an acetabular shell. The systems, devices and methods disclosed herein can reduce or eliminate the need for reliance on manually positioning of impaction instruments by utilizing a robotic surgical arm and the techniques discussed herein.

The above detailed description includes references to the accompanying drawings, which form a part of the detailed description. The drawings show, by way of illustration, specific embodiments in which the invention can be practiced. These embodiments are also referred to herein as "examples." Such examples can include elements in addition to those shown or described. However, the present inventors also contemplate examples in which only those elements shown or described are provided. Moreover, the present inventors also contemplate examples using any combination or permutation of those elements shown or described (or one or more aspects thereof), either with respect to a particular example (or one or more aspects thereof), or with respect to other examples (or one or more aspects thereof) shown or described herein. The Abstract is provided to comply with 37 C.F.R. § 1.72(b), to allow the reader to quickly ascertain the nature of the technical disclosure. It is submitted with the understanding that it will not be used to interpret or limit the scope or meaning of a claim. Also, in the above Detailed Description, various features may be grouped together to streamline the disclosure. This should not be interpreted as intending that an unclaimed disclosed feature is essential to any claim. Rather, inventive subject matter may lie in less than all features of a particular disclosed embodiment.

What is claimed is:

1. A method to robotically guide an instrument relative to the anatomy of a patient, the method comprising:
    acquiring a calibration image from a medical imaging device, the calibration image including a portion of the anatomy and an instrument end effector coupled to a robotic arm of a robotic surgical device in a first position and orientation relative to a coordinate system of the robotic surgical device, the instrument end effector including a cup-shaped element affixed to a distal end;
    identifying a first plurality of patient landmarks on the portion of the anatomy in the calibration image;
    identifying a first elliptical outline of an opening of the cup-shaped element in the calibration image;
    acquiring a navigation image from the medical imaging device, the navigation image including the portion of anatomy, the cup-shaped element and the instrument end effector at a second position and orientation;
    identifying a second plurality of patient landmarks on the portion of anatomy in the navigation image;
    identifying a second elliptical outline of the opening of the cup-shaped element in the navigation image;
    aligning the coordinate system of the robotic surgical device to a frame of reference of the anatomy of the patient using the first elliptical outline and the second elliptical outline;
    receiving, relative to the frame of reference of the anatomy of the patient, a target inclination and a target anteversion for placement of the cup-shaped element; and
    generate commands to guide the instrument end effector into a position and orientation to align the cup-shaped element to the target inclination and the target anteversion in reference to the anatomy of the patient.

2. The method of claim 1, wherein acquiring the calibration image includes receiving the calibration image on a handheld computing device from the medical imaging device.

3. The method of claim 1, wherein identifying the first plurality of patient landmarks include identifying a teardrop, a brim line, and an obturator foramen contour.

4. The method of claim 1, wherein identifying the first elliptical outline or the second elliptical outline of the opening of the cup-shaped element includes receiving a manual adjustment of a position, a size, or an orientation of the first elliptical outline or the second elliptical outline.

5. The method of claim 1, wherein identifying the first elliptical outline or the second elliptical outline of the opening of the cup-shaped element includes identifying a region-of-interest containing an elliptical contour using a Hough transform.

6. The method of claim 1, wherein aligning the coordinate system of the robotic surgical device to the frame of reference of the anatomy includes computing a first transformation between a first image position of the instrument end effector in coordinates of the calibration image and a second image position of the instrument end effector in coordinates of the navigation image.

7. The method of claim 6, wherein aligning the coordinate system of the robotic surgical device to the frame of reference of the anatomy includes computing a second transformation between a first robot position of the instrument end effector in coordinates of the coordinate system of the robotic surgical device and a second robot position of the instrument end effector in of the coordinate system of the robotic surgical device.

8. The method of claim 7, wherein aligning the coordinate system of the robotic surgical device to the frame of reference of the anatomy includes aligning the first transformation and the second transformation to register the navigation image in the coordinate system of the robotic surgical device.

9. The method of claim 1, wherein aligning the coordinate system of the robotic surgical device to the frame of reference of the anatomy includes aligning the calibration image and the navigation image using the first plurality of patient landmarks and the second plurality of patient landmarks.

10. The method of claim 9, wherein aligning the calibration image and the navigation image includes calculating a first angle between brim lines in the calibration image and the navigation image and calculating a second angle between teardrop to barycenter of foramen axes lines in the calibration image and navigation image.

11. The method of claim 10, wherein aligning the calibration image and the navigation image includes applying a rotation equal to an average of the first angle and the second angle.

12. The method of claim 11, wherein aligning the calibration image and the navigation image includes matching foramen contours and brim line points across the calibration image and the navigation image to determine scaling and rotation.

13. The method of claim 12, wherein matching foramen contours and brim line points includes using an iterative closest point algorithm to determine the scaling and rotation.

14. The method of claim 1, wherein acquiring the calibration image from the medical imaging device includes displaying an instruction to position the instrument end effector at a pre-defined inclination angle and a pre-defined anteversion angle relative to the anatomy of the patient.

15. The method of claim 14, wherein acquiring the navigation image from the medical imaging device includes displaying an instruction to position the instrument end effector at a second pre-defined inclination angle and a second anteversion angle relative to the anatomy of the patient.

16. The method of claim 1, further comprising registering the anatomy of the patient to an imaging coordinate system.

17. The method of claim 1, further comprising validating a target orientation of the cup-shaped element including validating inclination and anteversion.

18. A method comprising:
   determining a first acetabular cup elliptical outline within a first fluoroscopic image including an acetabular cup impaction instrument in a first position, the acetabular cup impaction instrument including an acetabular cup affixed to a distal end;
   determining a second acetabular cup elliptical outline within a second fluoroscopic image including the acetabular cup impaction instrument in a second position;
   aligning a robotic coordinate system to a target coordinate system associated with the first fluoroscopic image and the second fluoroscopic image using the first acetabular cup elliptical outline and the second acetabular cup elliptical outline, wherein the target coordinate system is one of a coordinate system relative to a fluoroscopic imaging device or a coordinate system relative to anatomy of the patient;
   receiving a target inclination and a target anteversion relative to the target coordinate system for impaction of the acetabular cup; and
   generating commands for a robotic arm to position the acetabular cup impaction instrument into a position and an orientation to align the acetabular cup to the target inclination and the target anteversion.

19. The method of claim 18, wherein the aligning the robotic coordinate system to the target coordinate system includes:
   calculating a first transformation between the first acetabular cup elliptical outline and the second acetabular cup elliptical outline;
   calculating a second transformation between the first position of the acetabular cup impaction instrument and the second position of the acetabular cup impaction instrument; and
   aligning the robotic coordinate system with the target coordinate system based on the first transformation and the second transformation.

20. A system comprising:
   a fluoroscope configured to capture fluoroscopic images of a portion of anatomy of a patient;
   an acetabular cup impaction instrument adapted to impact an acetabular cup into the acetabula of the patient;
   a robotic arm including an end effector adapted to position the acetabular cup impaction instrument for impaction of the acetabular cup; and
   a computing device including a processor and a memory device, the memory device including instructions that, when executed by the processor, cause the processor to perform operations including:
      determining a first acetabular cup ellipse within a first fluoroscopic image generated by the fluoroscope, the first fluoroscopic image including the acetabular cup impaction instrument in a first position, the acetabular cup impaction instrument including the acetabular cup affixed to a distal end;
      determining a second acetabular cup ellipse within a second fluoroscopic image generated by the fluoroscope, the second fluoroscopic image including the acetabular cup impaction instrument in a second position;
      aligning a coordinate system associated with the robotic arm to an image coordinate system associated with the fluoroscope using the first acetabular cup ellipse and the second acetabular cup ellipse;
      receiving a target inclination and a target anteversion for impaction of the acetabular cup; and
      generating commands for the robotic arm to position the acetabular cup impaction instrument into a position and an orientation to align the acetabular cup to the target inclination and the target anteversion.

* * * * *